United States Patent
Iwata et al.

(10) Patent No.: US 12,138,336 B2
(45) Date of Patent: *Nov. 12, 2024

(54) PERSONAL CARE COMPOSITION COMPRISING WATER INSOLUBLE SOLID ORGANIC COMPOUND

(71) Applicant: The Procter & Gamble Company, Cincinnati, OH (US)

(72) Inventors: Toshiyuki Iwata, Singapore (SG); Shikhar Gupta, Singapore (SG); Marco Klaehn, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/443,353

(22) Filed: Feb. 16, 2024

(65) Prior Publication Data

US 2024/0180806 A1     Jun. 6, 2024

Related U.S. Application Data

(63) Continuation of application No. 16/591,939, filed on Oct. 3, 2019, now Pat. No. 11,964,038.

(60) Provisional application No. 62/740,973, filed on Oct. 4, 2018.

(51) Int. Cl.
*A61K 8/49* (2006.01)
*A61K 8/92* (2006.01)
*A61Q 5/12* (2006.01)

(52) U.S. Cl.
CPC ............. *A61K 8/4926* (2013.01); *A61K 8/92* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 4,275,055 A | 6/1981 | Nachtigal et al. |
| 4,557,928 A | 12/1985 | Glover |
| 5,723,112 A | 3/1998 | Bowser et al. |
| 6,908,912 B2 | 6/2005 | Rioux et al. |
| 6,979,439 B1 | 12/2005 | Sakai et al. |
| 7,026,308 B1 | 4/2006 | Gavin et al. |
| 7,037,513 B1 | 5/2006 | Traynor et al. |
| 7,455,851 B1 | 11/2008 | Nelson et al. |
| 7,674,785 B2 | 3/2010 | Gavin et al. |
| 8,206,732 B2 | 6/2012 | Nelson et al. |
| 8,273,332 B2 | 9/2012 | Gross et al. |
| 8,796,252 B2 | 8/2014 | Rioux et al. |
| 9,132,289 B2 | 9/2015 | Kawai |
| 2002/0119326 A1 | 8/2002 | Zubkov et al. |
| 2004/0058855 A1 | 3/2004 | Schwartz et al. |
| 2004/0191331 A1 | 9/2004 | Schwartz et al. |
| 2004/0213751 A1 | 10/2004 | Schwartz et al. |
| 2006/0263402 A1 | 11/2006 | Deckner et al. |
| 2007/0104672 A1 | 5/2007 | Decoster et al. |
| 2007/0128147 A1 | 6/2007 | Schwartz et al. |
| 2007/0248551 A1 | 10/2007 | Lemoine et al. |
| 2007/0292380 A1 | 12/2007 | Staudigel et al. |
| 2008/0206355 A1 | 8/2008 | Schwartz et al. |
| 2010/0247472 A1 | 9/2010 | Sau |
| 2010/0322885 A1 | 12/2010 | Ueno |
| 2011/0028571 A1 | 2/2011 | Hayakawa |
| 2011/0294773 A1 | 12/2011 | Ishikubo et al. |
| 2012/0058071 A1 | 3/2012 | Gross et al. |
| 2012/0064137 A1 | 3/2012 | Kawai |
| 2012/0088807 A1 | 4/2012 | Krouse et al. |
| 2012/0251627 A1 | 10/2012 | Nelson et al. |
| 2012/0316239 A1 | 12/2012 | Okada et al. |
| 2013/0259817 A1 | 10/2013 | Uehara et al. |

(Continued)

FOREIGN PATENT DOCUMENTS

| | | |
|---|---|---|
| CN | 1277836 A | 12/2000 |
| CN | 1553796 A | 12/2004 |

(Continued)

OTHER PUBLICATIONS

All Office Actions; U.S. Appl. No. 14/174,389, filed Feb. 2, 2014.
All Office Actions; U.S. Appl. No. 14/174,401, filed Feb. 2, 2014.
All Office Actions; U.S. Appl. No. 14/174,433, filed Feb. 2, 2014.
All Office Actions; U.S. Appl. No. 16/591,939, filed Oct. 3, 2019.
Chemical Book Citronellol, URL: https://www.chemicalbook.com/ChemicalProductProperty_EN_CB3377987.htm, retrieved online on Aug. 27, 2021 (Year: 2021), 5 pages.

(Continued)

*Primary Examiner* — Jennifer A Berrios
(74) *Attorney, Agent, or Firm* — John G. Powell

(57) ABSTRACT

Disclosed is a personal care composition comprising: (a) a cationic or nonionic surfactant; (b) a high melting point fatty compound having a melting point of from 25oC to 60oC (c) a solid organic compound having a water solubility of lower than 25 g per 1 liter water, and having a melting point of exceeding 60oC, and also having a specific Alog P; (d) a first liquid oily compound other than a second liquid oily compound, wherein the first liquid oily compound has a water solubility of 10 g per 1 liter water or less, wherein a mixture of all the first liquid oily compounds included in the composition has a di-electric constant of from about 5 to about 10, and wherein the weight ratio of the solid organic compound to the first liquid oily compound is from about 1:1 to about 1:10; and (e) an aqueous carrier, wherein the composition comprises 0.1% or less of a second liquid oily compound having a higher AlogP of 7.0 or higher. The composition of the present invention provides improved deposition of the solid organic compound and/or reduced crystallization of the solid organic compound in the composition.

11 Claims, 1 Drawing Sheet

(56) References Cited

U.S. PATENT DOCUMENTS

| | | |
|---|---|---|
| 2013/0259820 A1 | 10/2013 | Snyder et al. |
| 2013/0276808 A1 | 10/2013 | Molenda et al. |
| 2013/0280193 A1 | 10/2013 | Carter et al. |
| 2014/0335040 A1 | 11/2014 | Yu et al. |
| 2014/0356401 A1 | 12/2014 | Yoshida et al. |
| 2015/0090285 A1* | 4/2015 | Worner ............... A61K 8/898 132/204 |
| 2015/0165690 A1 | 6/2015 | Tow |
| 2015/0216769 A1 | 8/2015 | Takahashi |
| 2015/0216770 A1 | 8/2015 | Takahashi et al. |
| 2015/0216774 A1 | 8/2015 | Yu et al. |
| 2015/0216777 A1 | 8/2015 | Takahashi |
| 2015/0216786 A1 | 8/2015 | Yu et al. |
| 2015/0216984 A1 | 8/2015 | Yu |
| 2016/0235651 A1 | 8/2016 | Decoster |
| 2016/0374431 A1 | 12/2016 | Tow |
| 2017/0105917 A1 | 4/2017 | Iwata |
| 2017/0105918 A1 | 4/2017 | Iwata |
| 2017/0105919 A1 | 4/2017 | Iwata |
| 2018/0200171 A1 | 7/2018 | Iwata |
| 2020/0108003 A1 | 4/2020 | Iwata et al. |

FOREIGN PATENT DOCUMENTS

| | | |
|---|---|---|
| CN | 1602835 A | 4/2005 |
| CN | 101984953 A | 3/2011 |
| CN | 101112349 B | 5/2011 |
| CN | 104080440 A | 10/2014 |
| CN | 107530231 A | 1/2018 |
| DE | 10259402 A1 | 7/2004 |
| DE | 10310381 A1 | 9/2004 |
| DE | 102012203240 A1 | 3/2013 |
| EP | 0060611 A2 | 9/1982 |
| EP | 0074819 A2 | 3/1983 |
| EP | 1527768 A1 | 5/2005 |
| EP | 1504744 B1 | 7/2010 |
| JP | S5865210 A | 4/1983 |
| JP | H02273611 A | 11/1990 |
| JP | H04108724 A | 4/1992 |
| JP | H09110652 A | 4/1997 |
| JP | 2001516705 A | 10/2001 |
| JP | 2007045726 A | 2/2007 |
| JP | 2007277227 A | 10/2007 |
| JP | 2007284459 A | 11/2007 |
| JP | 2008534626 A | 8/2008 |
| JP | 2010533704 A | 10/2010 |
| JP | 4955959 B2 | 6/2012 |
| KR | 20010045153 A | 6/2001 |
| WO | 9913844 A1 | 3/1999 |
| WO | 2007001844 A1 | 1/2007 |
| WO | 2008010177 A2 | 1/2008 |
| WO | 2009016555 A2 | 2/2009 |
| WO | 2010080543 A1 | 7/2010 |
| WO | 2011009710 A1 | 1/2011 |
| WO | 2012119825 A2 | 9/2012 |
| WO | 2013072163 A1 | 5/2013 |
| WO | 2014124066 A1 | 8/2014 |
| WO | 2014124070 A1 | 8/2014 |
| WO | 2015133382 A1 | 9/2015 |

OTHER PUBLICATIONS

Chemical Book Hexyl Cinnamic Aldehyde, URL: https://www.chemicalbook.com/ChemicalProductProperty_EN_CB2154127.htm, retrieved online on Aug. 27, 2021 (Year: 2021), 4 pages.

Extra Fullness Dandruff Condition; Database GNPD Mintel Jul. 2004, 4 pages.

Fevola, Michael J. "Polyquatermium-6", Cosmetics and toiletries 126.3 (Mar. 2011) 150-154.

GNPD Database—"2 in 1 Shampoo and Conditioner", Nov. 15, 2011, 3 pages.

GNPD database—"Anti Dandruff 2 in 1 Shampoo", Aug. 11, 2014, 3 pages.

GNPD Database—"Fortifying Anti-Dandruff Shampoo", Feb. 13, 2008, 2 pages.

Lubrizol Advanced Materials, Inc., "Merquat 106 Polymer Technical Datasheet", Nov. 1, 2011, 2 pages.

AA1314M PCT Search Report and Written Opinion for PCT/US2019/054425 dated Dec. 4, 2019, 10 pages.

The Metabolomics Innovation Centre, Citronellol, https://foodb.ca/compounds/FDB014490 Retrieved online Aug. 17, 2021 (Year: 2021), 7 pages.

* cited by examiner

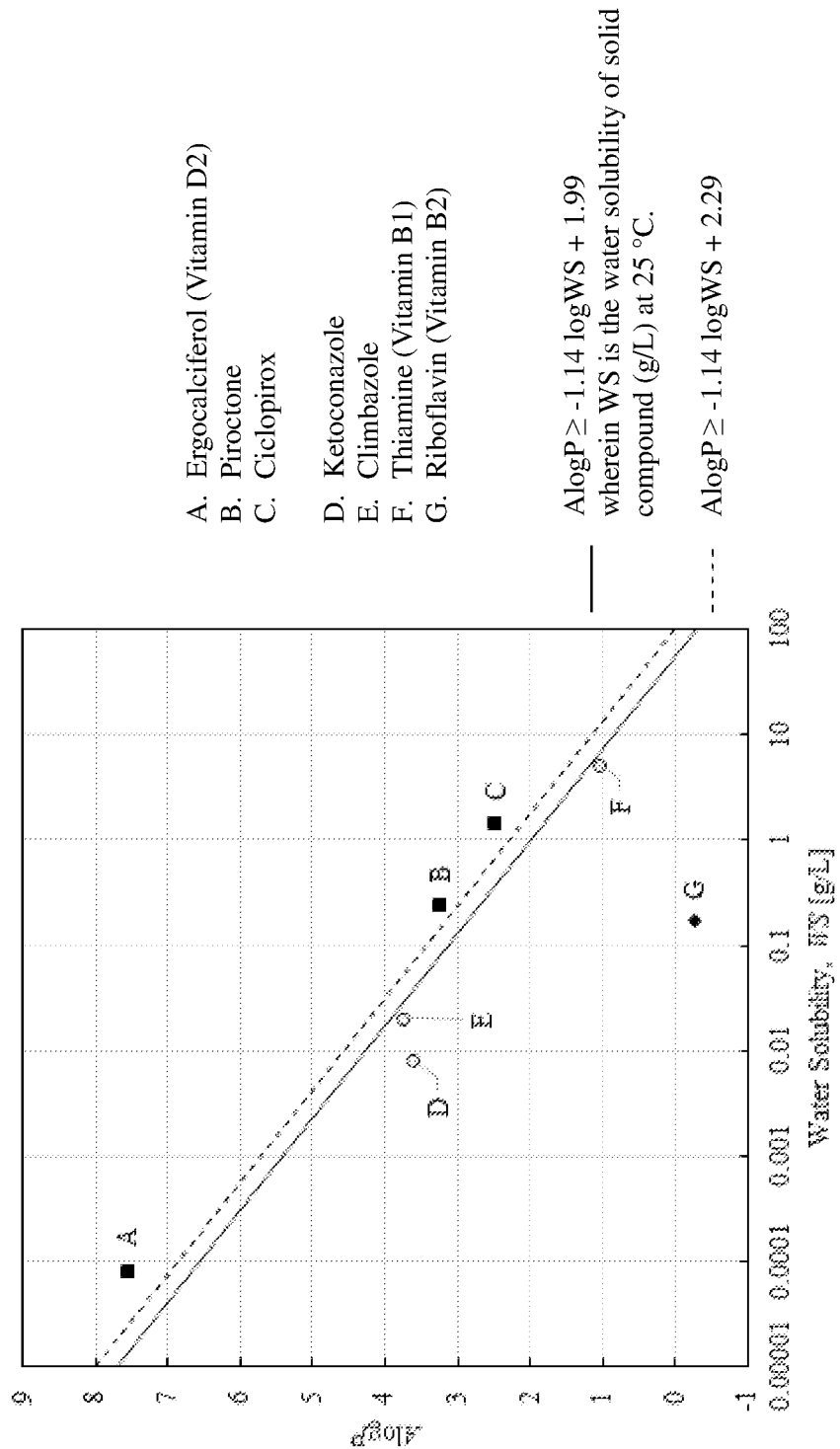

PERSONAL CARE COMPOSITION COMPRISING WATER INSOLUBLE SOLID ORGANIC COMPOUND

FIELD OF THE INVENTION

The present invention relates to a personal care composition comprising: (a) a cationic or nonionic surfactant; (b) a high melting point fatty compound having a melting point of from 25° C. to 60° C.; (c) a solid organic compound having a water solubility of lower than 25 g per 1 liter water, and having a melting point of exceeding 60° C., and also having a specific Alog P; (d) a first liquid oily compound other than a second liquid oily compound, wherein the first liquid oily compound has a water solubility of 10 g per 1 liter water or less, wherein a mixture of all the first liquid oily compounds included in the composition has a di-electric constant of from about 5 to about 10, and wherein the weight ratio of the solid organic compound to the first liquid oily compound is from about 1:1 to about 1:10; and (e) an aqueous carrier, wherein the composition comprises 0.1% or less of a second liquid oily compound having a higher AlogP of 7.0 or higher. The composition of the present invention provides improved deposition of the solid organic compound and/or reduced crystallization of the solid organic compound in the composition

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits. Furthermore, a variety of approaches have been developed to provide other benefits by benefit agents, in addition to such conditioning benefits.

Some of such benefit agents are solid organic compounds and have low solubility in water, thus, often hard to be dissolved in aqueous conditioning composition comprising above conditioning agents. Such solid benefit agents tend to form crystal in such aqueous conditioning composition, which may negatively affect product appearance, product texture, and/or human safety.

For example, Piroctone and salt of Piroctone such as Piroctone Olamine is known to provide antidandruff benefit. Piroctone Olamine is often supplied as crystal powders, and is also known to have very limited solubility in water but have some solubility in ethanol/water mixture, propylene glycol, etc. However, the present inventors have surprisingly found that, when such ethanol/water mixture dissolving piroctone olamine is added to aqueous hair conditioning compositions comprising cationic surfactant and high melting point fatty compounds, piroctone olamine forms crystals especially when piroctone olamine is contained at a higher amount.

The present inventors have found a need for personal care composition containing solid organic compounds as benefit agents, to provide reduced crystallization of such solid organic compounds. None of the existing art provides all of the advantages and benefits of the present invention.

SUMMARY OF THE INVENTION

The present invention is directed to a personal care composition comprising by weight:
(a) from about 0.1% to about 10% of a cationic or nonionic surfactant;
(b) from about 0.1% to about 20% of a high melting point fatty compound having a melting point of from 25° C. to 60° C.;
(c) from about 0.1% to about 2.0% of a solid organic compound having a water solubility of lower than 25 g per 1 liter water, and having a melting point of exceeding 60° C., and also having AlogP meeting the following method of calculation:

$$A \log P \geq -1.14 \log WS + 1.99$$

wherein WS stands for water solubility (g per 1 liter water at 25° C.);
(d) a first liquid oily compound other than a second liquid oily compound, wherein the first liquid oily compound has a water solubility of 10 g per 1 liter water or less, wherein a mixture of all the first liquid oily compounds included in the composition has a di-electric constant of from about 5 to about 10, and wherein the weight ratio of the solid organic compound to the first liquid oily compound is from about 1:1 to about 1:10; and
(e) an aqueous carrier,
wherein the composition comprises 0.1% or less of a second liquid oily compound having a higher AlogP of 7.0 or higher.

The composition of the present invention provides improved deposition of the solid organic compound, and/or reduced crystallization of the solid organic compound in the composition.

These and other features, aspects, and advantages of the present invention will become better understood from a reading of the following description, and appended claims.

BRIEF DESCRIPTION OF THE DRAWINGS

The FIGURE shows Alog P and WS for some of the solid organic compounds used in the present invention and some other solid compounds, along with the following calculation method: A log P≥−1.14 log WS+1.99 wherein WS stands for water solubility (g per 1 liter water at 25° C.).

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

The term "molecular weight" or "M.Wt." as used herein refers to the weight average molecular weight unless otherwise stated.

Personal Care Composition

The personal care composition of the present invention comprises by weight:
(a) from about 0.1% to about 10% of a cationic or nonionic surfactant;
(b) from about 0.1% to about 20% of a high melting point fatty compound having a melting point of from 25° C. to 60° C.;
(c) from about 0.1% to about 2.0% of a solid organic compound having a water solubility of lower than 25 g per 1 liter water, and having a melting point of exceeding 60° C., and also having AlogP meeting the following method of calculation:

A log P≥−1.14 log WS+1.99 wherein WS stands for water solubility (g per 1 liter water at 25° C.);
(d) a first liquid oily compound other than a second liquid oily compound, wherein the first liquid oily compound has a water solubility of 10 g per 1 liter water or less, wherein a mixture of all the first liquid oily compounds included in the composition has a di-electric constant of from about 5 to about 10, and wherein the weight ratio of the solid organic compound to the first liquid oily compound is from about 1:1 to about 1:10; and
(e) an aqueous carrier,
wherein the composition comprises 0.1% or less of a second liquid oily compound having a higher AlogP of 7.0 or higher.

It has been found by the present inventors that, when the solid organic compounds, especially Piroctone and/or salts thereof, tend to crystallize in the following conditions:
when the aqueous composition comprises cationic surfactant and high melting point fatty compounds
when the amount of the solid organic compounds increases in the composition, especially 0.2% or above;
wherein the weight ratio of the surfactant to the high melting point fatty compound is in the range of, preferably from about 1:1 to about 1:4, more preferably from about 1:1.5 to about 1:3.5; and/or
when the composition has pH of from about 3.5 to about 6.

It has also been found by the present inventors that by the use of a first liquid oily compound having a specific di-electric constant at a specific weight ratio to the solid organic compounds, the composition has reduced crystallization of the solid organic compounds while containing a higher level of the solid organic compounds. Thus, the composition of the present invention provides improved deposition of the solid organic compound on scalp.

These ingredients and features are explained below in detail.

The personal care composition is preferably selected from the group consisting of a hair care composition, a body care composition, a facial skin care composition, and mixtures thereof, and more preferably is a hair care composition.

Preferably, the composition of the present invention is substantially free of anionic surfactants in view of avoiding undesirable interaction with cationic surfactants and/or in view of stability of the gel matrix. In the present invention, "the composition being substantially free of anionic surfactants" means that: the composition is free of anionic surfactants; or, if the composition contains anionic surfactants, the level of such anionic surfactants is very low. In the present invention, the total level of such anionic surfactants is, if included, 1% or less, preferably 0.5% or less, more preferably 0.1% or less, still more preferably 0% by weight of the composition.

Preferably, the composition of the present invention contains limited amount of ethanol, for example, at a level of up to about 10%, more preferably up to about 5%, still more preferably up to about 1% by weight of the composition, even more preferably 0%, i.e., the composition is free of ethanol.

Solid Organic Compound

The composition of the present invention comprises a solid organic compound having:
a water solubility of lower than 25 g per 1 liter water, preferably lower than 10 g per 1 liter water, more preferably lower than 5 g per 1 liter water, still more preferably lower than 2 g per 1 liter water; and
a melting point of exceeding 60° C. (not including 60° C.), preferably 80° C. or more, more preferably 90° C. or more, still more preferably 95° C. or more.
Water solubility herein is measured at 25° C.
The solid organic compound has AlogP meeting the following method of calculation:

A log P≥−1.14 log WS+1.99 wherein WS stands for water solubility (g per 1 liter water at 25° C.).

Preferably, the solid organic compound has AlogP meeting the following method of calculation:

A log P≥−1.14 log WS+1.99

The solid organic compound may have AlogP of 0 or more, preferably 1 or more, more preferably 2 or more. "AlogP" as used herein, is an identification of the octanol-water partition coefficient of an active. Ghose and Crippen used this atom-based method to calculate the octanol-water partition coefficient (log P), and the molar refractivity (MR) for incoming molecules. Log P provides a measure of the hydrophobicity of the molecule, while MR contains information about molecular volume and polarizability. AlogP is calculated herein using Pipeline Pilot software (Biovia™) ver 9.2.

The solid organic compound is contained in the composition at a level by weight of the composition, of from about 0.1% to about 2.0%, preferably from about 0.2% to about 1.0%, more preferably from about 0.22% to about 1.0%.

Such solid organic compounds include, for example, those in the below table.

| | ALogP | Water Solubility (g/L) | m.p./° C. |
|---|---|---|---|
| Piroctone Olamine | Refer to Piroctone | $3.00 \times 10^{-2}$ | 136 |
| Piroctone | 3.251 | $2.40 \times 10^{-1}$ | 108 |
| Ciclopirox Olamine | Refer to Ciclopirox | 4.45 | 152-156 |
| Ciclopirox | 2.49 | 1.41 | 143 |
| Ergocalciferol (vitamin D2) | 7.563 | $8.15 \times 10-5$ | 114 |

Piroctone Olamine and Ciclopirox Olamine are the salt of Piroctone and Ciclopirox, respectively, with Monoethanolamine. In the compositions having an acidic pH, they become protonated to become Piroctone and Ciclopirox, respectively. In the present invention, the composition preferably has an acidic pH, more preferably has a pH from about 2 to about 6, still more preferably from about 3.5 to about 6, further more preferably from about 3.5 to about 5.

Within the diverse class of such solid organic compounds, preferred are Piroctone and salts thereof and Cyclopirox and salts thereof, and more preferred are Piroctone and salts thereof, which salts includes, for example, Piroctone Olamine which is a salt of Piroctone and monoethanolamine.

First Liquid Oily Compound

The composition of the present invention comprises a first liquid oily compound other than a second liquid oily compound, the first liquid oily compound having:
- a water solubility of 10 g or less per 1 liter water, preferably 5 g or less per 1 letter water, more preferably 2 g or less per 1 liter water.
- wherein a mixture of all the first liquid oily compounds included in the composition has a di-electric constant (DC) of from about 5 to about 10, preferably from about 6 to about 9, more preferably from about 7 to about 9.

Dielectric constant is measured at room temperature (23.1 ~23.4° C.) using BI-870 Liquid Dielectric Constant Meter (Brookhaven Instruments, Corp., New York).

The first liquid oily compound may have a lower AlogP from about 1 to 6.0, preferably from about 1.5 to 6.0, more preferably from about 2.0 to 5.5.

The weight ratio of the solid organic compound to the first liquid oily compound is from about 1:1 to about 1:10, preferably from about 1:1.2 to about 1:10, more preferably from about 1:1.5 to about 1:10.

The first liquid oily compound can be contained in the composition at a level by weight of the composition, of preferably from about 0.2% to about 5%, more preferably from about 0.2% to about 3%, still more preferably from about 0.3% to about 2%.

Such first liquid oily compounds are preferably different from liquid silicone compounds, and include, for example, those in the below table.

| Chemical | Solubility in H$_2$O (g/L) | AlogP |
|---|---|---|
| Isoropyl N-Lauroyl Sarcosinate | Negligible (lower than 0.1) | 4.8 |
| Dihydro Myrcenol | Negligible (lower than 0.1) | 2.8 |
| Hexyl Cinnamic Aldehyde | $2.75 \times 10^{-3}$ | 4.7 |
| Hexyl Salicylate | $9.00 \times 10^{-3}$ | 3.7 |
| Galoxolide | $2.94 \times 10^{-4}$ | 4.3 |
| Methyl Dihydro Jasmonate | $9.17 \times 10^{-2}$ | 2.8 |
| Linalool | 1.6 | 2.7 |
| Limonene | $1.38 \times 10^{-2}$ | 3.5 |
| Hexyl Cinnamal (=Hexyl Cinnamic Aldehyde) | $2.75 \times 10^{-3}$ | 4.7 |

Second Liquid Oily Compound

The composition of the present invention comprises 0.1% or less of a second liquid oily compound having an AlogP of 7.0 or more, preferably 6.7 or more, more preferably 6.1 or more, still more preferably 5.6 or more. Preferably, the composition comprises 0.05% or less of the second liquid oily compound, more preferably the composition comprises 0.01% or less of the second liquid oily compound, and still more preferably the composition is free of the second liquid oily compound, in view of providing reduced oily feel to hair, face, body and/or hands.

Such second liquid oily compounds are different from liquid silicone compounds. Some of such second liquid oily compounds and some other liquid compounds having relatively higher AlogP compared to the first liquid oily compound are exemplified in the below table.

| Chemical | AlogP |
|---|---|
| Triethylhexanoin | 8.6 |
| Isostearyl Alcohol | 7.2 |
| Isopropyl Palmitate | 7.3 |
| Isopropyl Isostearate | 8.1 |
| C11-12 Isoparaffin | 6.1 |
| PPG-15 Stearyl Ether | 7.6 |
| Squalane | 12.8 |
| Cetyl Esters (hexadecyl hexadecanoate) | 13.4 |
| Octyldodecyl Myristate | 14.2 |

The present inventors have found that, some of the second liquid oily compounds having higher AlogP may help the reduction of crystallization of the solid organic compounds in the compositions, however, they tend to be included at a higher concentration in the composition for such crystallization reduction of the solid organic compounds and also they tend to provide oily feel to hair, face, body and/or hands. Oily feel to hair can be also perceived as, for example, reduced free flowing of the hair.

Third Liquid Compound

Preferably, the composition further comprises a third liquid compound having a AlogP from about 1 to 6.0 and a water solubility of exceeding 10 g per 1 letter water (not including 10 g) to 50 g per 1 letter water.

Such third liquid compound can be contained in the composition at a level by weight of the composition of preferably from about 0.1% to about 2%, more preferably from about 0.2% to about 1.6%.

Such third liquid compounds are different from liquid silicone compounds, and include, for example, those in the below table.

| Chemical | Solubility in H2O (g/L) | AlogP | Di-electric constant |
|---|---|---|---|
| Benzyl Alcohol | 43.0 | 1.2 | 13.69 |
| Phenoxyethanol | 26.0 | 1.3 | 11.04 |

Cationic or Nonionic Surfactant

The composition of the present invention comprises a cationic or nonionic surfactant, preferably cationic surfactant.

The surfactant is included in the composition at a level by weight of preferably from about 0.1% to about 10%, more preferably from about 0.5% to about 8%, still more preferably from about 0.8% to about 5%, even more preferably from about 1.0% to about 4%.

Cationic Surfactant

The cationic surfactant can be one cationic surfactant or a mixture of two or more cationic surfactants. Preferably, the cationic surfactant system is selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt. More preferably, the cationic surfactant system is a mixture of mono-long alkyl quaternized ammonium salt and di-long alkyl quaternized ammonium salt.

Mono-Long Alkyl Quaternized Ammonium Salt

The monoalkyl quaternized ammonium salt cationic surfactants useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

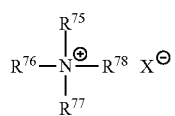

(I)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as ℓ-glutamic acid, lactic acid, hydrochloric acid, malic acid, succinic acid, acetic acid, fumaric acid, tartaric acid, citric acid, ℓ-glutamic hydrochloride, maleic acid, and mixtures thereof; more preferably ℓ-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Di-Long Alkyl Quaternized Ammonium Salt

Di-long alkyl quaternized ammonium salt is preferably combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of preferably from about 10% to about 50%, more preferably from about 30% to about 45%.

The dialkyl quaternized ammonium salt cationic surfactants useful herein are those having two long alkyl chains having 12-30 carbon atoms, preferably 16-24 carbon atoms, more preferably 18-22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

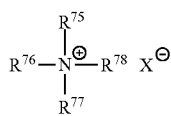

(II)

wherein two of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

High Melting Point Fatty Compound

The composition of the present invention comprises a high melting point fatty compound. The high melting point fatty compound is included in the composition at a level of preferably from about 0.1% to about 20%, more preferably from about 1% to about 15%, still more preferably from about 1.5% to about 8% by weight of the composition, The high melting point fatty compound useful herein have a melting point of 25° C. or higher to 60° C., preferably a melting point of 30° C. to 60° C., and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability when the consumer rinses off the composition.

Aqueous Carrier

The conditioning composition of the present invention comprises an aqueous carrier. The level and species of the carrier are selected according to the compatibility with other components, and other desired characteristics of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 30% to about 95%, and more preferably from about 80% to about 95% water.

Gel Matrix

Preferably, in the composition of the present invention, a cationic surfactant, a high melting point fatty compound, and an aqueous carrier form a gel matrix.

The gel matrix is suitable for providing various conditioning benefits, for example, hair conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6. For improved deposition of the solid organic compound on hair, face, body and/or scalp, it may be preferred that the weight ratio of the cationic surfactant to the high melting point fatty compound is in the range of, preferably from about 1:1 to about 1:4, more preferably from about 1:1.5 to about 1:3.5.

Silicone Compound

The compositions of the present invention may comprise a silicone compound. The silicone compound can be contained in the composition at a level of from about 0.05% to about 15%, preferably from about 0.1% to about 10%, more preferably from about 0.15% to about 5%, and even more preferably from about 0.2% to about 4% by weight of the composition.

Silicone Polymer Containing Quaternary Ammonium Groups

Such silicone compounds useful herein may be those having an amine or a quaternary ammonium group; and an alkylene oxide group, for example, Trideceth-9-amodimethicone, Silicone Quaternium-22. and those described below in detail.

Silicone compounds useful herein include, for example, a Silicone Polymer Containing Quaternary Groups comprising terminal ester groups, having a viscosity up to 100,000 mPa·s and a D block length of greater than 200 D units. Without being bound by theory, this low viscosity silicone polymer provides improved conditioning benefits, for example, hair conditioning benefits such as smooth feel, reduced friction, and prevention of hair damage, while eliminating the need for a silicone blend.

Structurally, the silicone polymer is a polyorganosiloxane compound comprising one or more quaternary ammonium groups, at least one silicone block comprising greater than 200 siloxane units, at least one polyalkylene oxide structural unit, and at least one terminal ester group. In one or more embodiments, the silicone block may comprise between 300 to 500 siloxane units.

In a preferred embodiment, the polyorganosiloxane compounds have the general formulas (Ia) and (Ib):

M-Y—[—($N^+R_2$-T-$N^+R_2$)—Y—]$_m$—[—($NR^2_2$-A-E-A'-$NR^2_2$)—Y—]$_k$-M  (Ia)

M-Y—[—($N^+R_2$-T-$N^+R_2$)—Y—]$_m$—[—($N^+R^2_2$-A-E-A'-$N^+R^2_2$)—Y—]$_k$-M  (Ib)

wherein:
  m is >0, preferred 0.01 to 100, more preferred 0.1 to 100, even more preferred 1 to 100, specifically 1 to 50, more specifically 1 to 20, even more specifically 1 to 10,
  k is 0 or an average value of from >0 to 50, or preferably from 1 to 20, or even more preferably from 1 to 10,
  M represents a terminal group, comprising terminal ester groups selected from

—OC(O)—Z

—OS(O)$_2$—Z

—OS(O$_2$)O—Z

—OP(O)(O—Z)OH

—OP(O)(O—Z)$_2$ wherein Z is selected from monovalent organic residues having up to 40 carbon atoms, optionally comprising one or more hetero atoms.

A and A' each are independently from each other selected from a single bond or a divalent organic group having up to 10 carbon atoms and one or more hetero atoms, and E is a polyalkylene oxide group of the general formula:

—[$CH_2CH_2O$]$_q$—[$CH_2CH(CH_3)O$]$_r$—[$CH_2CH(C_2H_5)O$]$_s$— wherein q=0 to 200, r=0 to 200, s=0 to 200, and q+r+s=1 to 600.

$R^2$ is selected from hydrogen or R,
R is selected from monovalent organic groups having up to 22 carbon atoms and optionally one or more heteroatoms, and wherein the free valencies at the nitrogen atoms are bound to carbon atoms,
Y is a group of the formula:

—K—S—K— and -A-E-A'- or -A'-E-A-, with

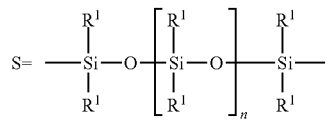

wherein $R^1$=$C_1$-$C_{22}$-alkyl, $C_1$-$C_{22}$-fluoralkyl or aryl; n=200 to 1000, and these can be identical or different if several S Groups are present in the polyorganosiloxane compound.

K is a bivalent or trivalent straight chain, cyclic and/or branched $C_2$-$C_{40}$ hydrocarbon residue which is optionally interrupted by —O—, —NH—, trivalent N, —$NR^1$—, —C(O)—, —C(S)—, and optionally substituted with —OH, wherein $R^1$ is defined as above, T is selected from a divalent organic group having up to 20 carbon atoms and one or more hetero atoms.

The residues K may be identical or different from each other. In the —K—S—K-moiety, the residue K is bound to the silicon atom of the residue S via a C—Si-bond.

Due to the possible presence of amine groups (—($NR^2$-A-E-A'-$NR^2$)—) in the polyorganosiloxane compounds, they may have protonated ammonium groups, resulting from the protonation of such amine groups with organic or inorganic acids. Such compounds are sometimes referred to as acid addition salts of the polyorganosiloxane compounds.

In a preferred embodiment the molar ratio of the quaternary ammonium groups b) and the terminal ester groups c) is less than 100:20, even more preferred is less than 100:30 and is most preferred less than 100:50. The ratio can be determined by $^{13}$C-NMR.

In a further embodiment, the polyorganosiloxane composition may comprise:
  A) at least one polyorganosiloxane compound, comprising a) at least one polyorganosiloxane group, b) at least one quaternary ammonium group, c) at least one terminal ester group, and d) at least one polyalkylene oxide group (as defined before),
  B) at least one polyorganosiloxane compound, comprising at least one terminal ester group, different from compound A).

In the definition of component A) it can be referred to the description of the polyorganosiloxane compounds of the invention. The polyorganosiloxane compound B) differs from the polyorganosiloxane compound A) preferably in that it does not comprise quaternary ammonium groups. Preferred polyorganosiloxane compounds B) result from the reaction of monofunctional organic acids, in particular carboxylic acids, and polyorganosiloxane containing bisepoxides.

In the polyorganosiloxane compositions the weight ratio of compound A) to compound B) is preferably less than 90:10. Or in other words, the content of component B) is at least 10 weight percent. In a further preferred embodiment of the polyorganosiloxane compositions in compound A) the molar ratio of the quaternary ammonium groups b) and the terminal ester groups c) is less than 100:10, even more preferred is less than 100:15 and is most preferred less than 100:20.

The silicone polymer has a viscosity at 20° C. and a shear rate of 0.1 s$^{-1}$ (plate-plate system, plate diameter 40 mm, gap width 0.5 mm) of less than 100,000 mPa·s (100 Pa·s). In further embodiments, the viscosities of the neat silicone polymers may range from 500 to 100,000 mPa·s, or preferably from 500 to 70,000 mPa·s, or more preferably from 500 to 50,000 mPa·s, or even more preferably from 500 to 20,000 mPa·s. In further embodiments, the viscosities of the neat polymers may range from 500 to 10,000 mPa·s, or preferably 500 to 5000 mPa·s determined at 20° C. and a shear rate of 0.1 s$^{-1}$.

In addition to the above listed silicone polymers, the following preferred compositions are provided below. For example, in the polyalkylene oxide group E of the general formula:

—[$CH_2CH_2O$]$_q$—[$CH_2CH(CH_3)O$]$_r$—[$CH_2CH(C_2H_5)O$]$_s$— wherein the q, r, and s indices may be defined as follows:
  q=0 to 200, or preferably from 0 to 100, or more preferably from 0 to 50, or even more preferably from 0 to 20,
  r=0 to 200, or preferably from 0 to 100, or more preferably from 0 to 50, or even more preferably from 0 to 20, s=0 to 200, or preferably from 0 to 100, or more preferably from 0 to 50, or even more preferably from 0 to 20, and q+r+s=1 to 600, or preferably from 1 to 100, or more preferably from 1 to 50, or even more preferably from 1 to 40.

For polyorganosiloxane structural units with the general formula S:

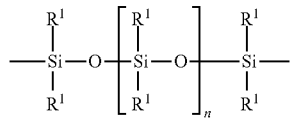

$R^1$=$C_1$-$C_{22}$-alkyl, $C_1$-$C_{22}$-fluoralkyl or aryl; n=from 200 to 1000, or preferably from 300 to 500, K (in the group —K—S—K—) is preferably a bivalent or trivalent straight chain, cyclical or branched $C_2$-$C_{20}$ hydrocarbon residue which is optionally interrupted by —O—, —NH—, trivalent N, —$NR^1$—, —C(O)—, —C(S)—, and optionally substituted with —OH.

In specific embodiments, $R^1$ is $C_1$-$C_{18}$ alkyl, $C_1$-$C_{18}$ fluoroalkyl and aryl. Furthermore, $R^1$ is preferably $C_1$-$C_{18}$ alkyl, $C_1$-$C_6$ fluoroalkyl and aryl. Furthermore, $R^1$ is more preferably $C_1$-$C_6$ alkyl, $C_1$-$C_6$ fluoroalkyl, even more preferably $C_1$-$C_4$ fluoroalkyl, and phenyl. Most preferably, $R^1$ is methyl, ethyl, trifluoropropyl and phenyl.

As used herein, the term "$C_1$-$C_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl moieties serve as examples.

Further as used herein, the term "$C_1$-$C_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are suitable examples.

Moreover, the term "aryl" means unsubstituted or phenyl substituted once or several times with OH, F, Cl, $CF_3$, $C_1$-$C_6$ alkyl, $C_1$-$C_6$ alkoxy, $C_3$-$C_7$ cycloalkyl, $C_2$-$C_6$ alkenyl or phenyl. Aryl may also mean naphthyl.

For the embodiments of the polyorganosiloxanes, the positive charges resulting from the ammonium group(s), are neutralized with inorganic anions such as chloride, bromide, hydrogen sulfate, sulfate, or organic anions, like carboxylates deriving from $C_1$-$C_{30}$ carboxylic acids, for example acetate, propionate, octanoate, especially from $C_{10}$-$C_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be, inter alia, modified based upon the selection of acids used.

The quaternary ammonium groups are usually generated by reacting the di-tertiary amines with an alkylating agents, selected from in particular di-epoxides (sometimes referred to also as bis-epoxides) in the presence of mono carboxylic acids and difunctional dihalogen alkyl compounds.

In a preferred embodiment the polyorganosiloxane compounds are of the general formulas (Ia) and (Ib):

M—Y—[—($N^+R_2$-T-$N^+R_2$)—Y—]$_m$—[—($NR^2$-A-E-A'-$NR^2$)—Y—]$_k$-M  (Ia)

M—Y—[—($N^+R_2$-T-$N^+R_2$)—Y—]$_m$—[—($N^+R^2_2$-A-E-A'-$N+R^2_2$)—Y—]$_k$-M  (Ib)

wherein each group is as defined above; however, the repeating units are in a statistical arrangement (i.e., not a block-wise arrangement).

In a further preferred embodiment the polyorganosiloxane compounds may be also of the general formulas (IIa) or (IIb):

M—Y—[—$N^+R_2$—Y—]$_m$—[—($NR^2$-A-E-A'-$NR^2$)—Y—]$_k$-M  (IIa)

M—Y—[—$N^+R_2$—Y—]$_m$—[—($N^+R^2_2$-A-E-A'-$N+R^2_2$)—Y—]$_k$-M  (IIb)

wherein each group is as defined above. Also, in such formula the repeating units are usually in a statistical arrangement (i.e not a block-wise arrangement).

wherein, as defined above, M is

—OC(O)—Z,

—OS(O)$_2$—Z

—OS(O$_2$)O—Z

—OP(O)(O—Z)OH

—OP(O)(O—Z)$_2$

Z is a straight chain, cyclic or branched saturated or unsaturated $C_1$-$C_{20}$, or preferably $C_2$ to $C_{18}$, or even more preferably a hydrocarbon radical, which can be interrupted by one or more —O—, or —C(O)— and substituted with —OH. In a specific embodiment, M is —OC(O)—Z resulting from normal carboxylic acids in particular with more than 10 carbon atoms like for example dodecanoic acid.

In a further embodiment, the molar ratio of the polyorganosiloxane-containing repeating group —K—S—K— and the polyalkylene repeating group -A-E-A'- or -A'-E-A- is between 100:1 and 1:100, or preferably between 20:1 and 1:20, or more preferably between 10:1 and 1:10.

In the group —($N^+R_2$-T-$N^+R^2$)—, R may represent a monovalent straight chain, cyclic or branched $C_1$-$C_{20}$ hydrocarbon radical, which can be interrupted by one or more —O—, —C(O)— and can be substituted by —OH, T may represent a divalent straight-chain, cyclic, or branched $C_1$-$C_{20}$ hydrocarbon radical, which can be interrupted by —O—, —C(O)— and can be substituted by hydroxyl.

The above described polyorganosiloxane compounds comprising quaternary ammonium functions and ester functions may also contain: 1) individual molecules which contain quaternary ammonium functions and no ester functions; 2) molecules which contain quaternary ammonium functions and ester functions; and 3) molecules which contain ester functions and no quaternary ammonium functions. While not limited to structure, the above described polyorganosiloxane compounds comprising quaternary ammonium functions and ester functions are to be understood as mixtures of molecules comprising a certain averaged amount and ratio of both moieties.

Various monofunctional organic acids may be utilized to yield the esters. Exemplary embodiments include $C_1$-$C_{30}$ carboxylic acids, for example $C_2$, $C_3$, $C_8$ acids, $C_{10}$-

$C_{18}$ carboxylic acids, for example $C_{12}$, $C_{14}$, $C_{16}$ acids, saturated, unsaturated and hydroxyl functionalized $C_{18}$ acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

Other Silicones

Such other silicones useful herein can be, for example, volatile silicones such as cyclic silicones, dimethylpolysiloxane fluid, dimethylpolysiloxane gum, amino silicone, and silicone copolyol. Preferred aminosilicones include, for example, those which conform to the general formula (I):

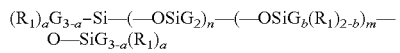

$$(R_1)_a G_{3-a}\text{-Si}\text{---}(\text{---OSiG}_2)_n\text{---}(\text{---OSiG}_b(R_1)_{2-b})_m\text{---}O\text{---SiG}_{3-a}(R_1)_a$$

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R^1$ is a monovalent radical conforming to the general formula $C_qH_{2q}L$, wherein q is an integer having a value from 2 to 8 and L is selected from the following groups: —N(R$_2$)CH$_2$—CH$_2$—N(R$_2$)$_2$; —N(R$_2$)$_2$; —N(R$_2$)$_3$A$^-$; —N(R$_2$)CH$_2$—CH$_2$—NR$_2$H$_2$A$^-$; wherein R$_2$ is hydrogen, phenyl, benzyl, or a saturated hydrocarbon radical, preferably an alkyl radical from about $C_1$ to about $C_{20}$; A$^-$ is a halide ion.

Highly preferred amino silicones are those corresponding to formula (I) wherein m=0, a=1, q=3, G=methyl, n is preferably from about 1500 to about 1700, more preferably about 1600; and L is —N(CH$_3$)$_2$ or —NH$_2$, more preferably —NH$_2$. Another highly preferred amino silicones are those corresponding to formula (I) wherein m=0, a=1, q=3, G=methyl, n is preferably from about 400 to about 600, more preferably about 500; and L is —N(CH$_3$)$_2$ or —NH$_2$, more preferably —NH$_2$. Such highly preferred amino silicones can be called as terminal aminosilicones, as one or both ends of the silicone chain are terminated by nitrogen containing group.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolyzed collagen with tradename Peptein 2000 available from Hormel, vitamin E with tradename Emix-d available from Eisai, panthenol available from Roche, panthenyl ethyl ether available from Roche, hydrolyzed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; perfumes; and sequestering agents, such as disodium ethylenediamine tetra-acetate; and ultraviolet and infrared screening and absorbing agents such as octyl salicylate.

Product Forms

The compositions of the present invention can be in the form of rinse-off products or leave-on products, and can be formulated in a wide variety of product forms, including but not limited to creams, gels, emulsions, mousses and sprays.

The conditioning composition of the present invention is especially suitable for rinse-off hair conditioner. Such compositions are preferably used by following steps:
  (i) after shampooing hair, applying to the hair an effective amount of the conditioning compositions for conditioning the hair; and
  (ii) then rinsing the hair.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Compositions (wt %)

TABLE 1

| Components | Ex. 1 | Ex. 2 | Ex. 3 | CEx. i | CEx. ii | CEx. iii | CEx. iv |
| --- | --- | --- | --- | --- | --- | --- | --- |
| 80% Behenyl trimethylammonium Chloride/ 20% Isopropyl alcohol | 3.42 | | 3.252 | 3.42 | | 2.85 | 3.42 |
| Stearylamidopropyl dimethylamine | | 2.4 | | | 2.4 | | |
| Polysorbate 20 | 0.03 | | | | | 0.03 | 0.03 |
| L-glutamic acid | | 0.768 | | | 0.768 | | |
| Citric acid | 0.22 | 0.3 | 0.2 | 0.22 | 0.3 | 0.22 | 0.22 |
| Cetyl alcohol | 1.67 | 2.5 | 2.5 | 1.67 | 2.5 | 1.67 | 1.67 |
| Stearyl alcohol | 4.18 | 4.5 | 4.5 | 4.18 | 4.5 | 4.18 | 4.18 |
| Sodium benzoate | 0.25 | 0.25 | 0.25 | 0.25 | 0.25 | 0.25 | 0.25 |
| Phenoxyethanol | 0.4 | 0.4 | 0.4 | 0.4 | 0.4 | 0.4 | 0.4 |
| Benzyl Alcohol | 0.4 | 0.4 | 0.4 | 0.4 | 0.4 | 0.4 | 0.4 |

TABLE 1-continued

| Components | Ex. 1 | Ex. 2 | Ex. 3 | CEx. i | CEx. ii | CEx. iii | CEx. iv |
|---|---|---|---|---|---|---|---|
| Piroctone Olamine | 0.25 | 0.25 | 0.25 | 0.25 | 0.25 | 0.25 | 0.25 |
| Perfume A (DC = 8.20), which is a mixture of the first oily compounds | 0.60 | | | | | 0.60 | 0.60 |
| Perfume B (DC = 8.10), which is a mixture of the first oily compounds | | 0.45 | 0.45 | | | | |
| Triethylhexanoin, which is the second oily compound | | | | | | | 2.5 |
| Octyldodecyl Myristate, which is the second oily compound | | | | | | 2.5 | |
| Silicone compound-P *1 | | 0.50 | 0.50 | | 0.50 | | |
| Silicone compound-T *2 | 0.50 | | | 0.50 | | 0.50 | 0.50 |
| Water | q.s. to 100% | q.s. to 100% | q.s. to 100% | q.s. to 100% | q.s. to 100% | q.s. to 100% | q.s. to 100% |
| Weight ratio of the solid organic compound to the first liquid oily compound = 1:X | 2.4 | 1.8 | 1.8 | 0.0 | 0.0 | 2.4 | 2.4 |
| pH | 4.1 | 4.5 | 4.1 | 4.0 | 4.4 | 4.5 | 4.2 |
| Crystals present at 25° C. or Not | No | No | No | Yes | Yes | No | No |
| Deposition of solid organic compound to Scalp (μg/cm$^2$) | 3.3 | 2.3 | 2.6 | 0.9 | 0.8 | n/a | n/a |
| Free flow/Pendulum Average Area Load (gf) | 1.58A | 1.47AB | n/a | n/a | 1.40BC | 1.08D | 0.87E |

TABLE 2

| Components | Ex. 4 | Ex. 5 | Ex. 6 | CEx. v |
|---|---|---|---|---|
| 80% Behenyl trimethylammonium Chloride/20% Isopropyl alcohol | | 3.42 | 3.42 | 3.42 |
| Stearylamidopropyl dimethylamine | 2.4 | | | |
| Polysorbate 20 | | 0.03 | 0.03 | 0.03 |
| L-glutamic acid | 0.768 | | | |
| Citric acid | 0.2 | 0.22 | 0.22 | 0.22 |
| Cetyl alcohol | 2.5 | 1.67 | 1.67 | 1.67 |
| Stearyl alcohol | 4.5 | 4.18 | 4.18 | 4.18 |
| Sodium benzoate | 0.25 | 0.25 | 0.25 | 0.25 |
| Phenoxyethanol | 0.4 | 0.4 | 0.4 | 0.4 |
| Benzyl Alcohol | 0.4 | 0.4 | 0.4 | 0.4 |
| Piroctone Olamine | 0.25 | 0.25 | 0.25 | 0.25 |
| Perfume A (DC = 8.20), which is a mixture of the first oily compounds | 0.60 | | | |
| Perfume C (DC = 9.44), which is a mixture of the first oily compounds | | 1.00 | | |
| Perfume D (DC = 7.44), which is a mixture of the first oily compounds | | | 2.50 | |
| Triethylhexanoin, which is the second oily compound | | | | 1.5 |
| Silicone compound-P *1 | 0.50 | | | |
| Silicone compound-T *2 | | 0.50 | 0.50 | 0.50 |
| Water | q.s. to 100% | q.s. to 100% | q.s. to 100% | q.s. to 100% |
| Weight ratio of the solid organic compound to the first liquid oily compound = 1:X | 2.4 | 4.0 | 10.0 | 0.0 |
| pH | 4.9 | 4.2 | 4.3 | 4.1 |
| Crystals present at 25° C. or Not | No | No | No | Yes |

TABLE 3

| Components | Ex. 7 | Ex. 8 | Ex. 9 | CEx. vi | CEx. vii |
|---|---|---|---|---|---|
| 80% Behenyl trimethylammonium Chloride/20% Isopropyl-alcohol | 3.42 | 3.42 | 3.42 | 3.42 | 3.42 |
| Polysorbate 20 | 0.03 | 0.03 | 0.03 | 0.03 | 0.03 |
| Citric acid | 0.22 | 0.22 | 0.22 | 0.22 | 0.22 |
| Cetyl alcohol | 1.67 | 1.67 | 1.67 | 1.67 | 1.67 |
| Stearyl alcohol | 4.18 | 4.18 | 4.18 | 4.18 | 4.18 |
| Sodium benzoate | 0.25 | 0.25 | 0.25 | 0.25 | 0.25 |
| Phenoxyethanol | 0.4 | 0.4 | 0.4 | 0.4 | 0.4 |
| Benzyl Alcohol | 0.4 | 0.4 | 0.4 | 0.4 | 0.4 |
| Ciclopirox Olamine | 0.25 | 1.00 | | 1.00 | |
| Ergocalciferol (vitamin D2) | | | 0.25 | | 0.25 |
| Perfume A (DC = 8.20), which is a mixture of the first oily compounds | 0.60 | 2.00 | 0.60 | | |
| Silicone compound-T *2 | 0.50 | 0.50 | 0.50 | 0.50 | 0.50 |
| Water | q.s. to 100% | q.s. to 100% | q.s. to 100% | q.s. to 100% | q.s. to 100% |
| Weight ratio of the solid organic compound to the first liquid oily compound = 1:X | 2.4 | 2.0 | 2.4 | 0.0 | 0.0 |
| pH | 4.0 | 4.3 | 3.4 | 4.2 | 3.5 |
| Crystals present at 25° C. or Not | No | No | No | Yes | Yes |

Definitions of Components

*1 Polydimethylsiloxane, having a viscosity 10,000 mPa · s

*2 Available from Momentive having a viscosity 10,000 mPa · s, and having following formula (I):

$(R_1)_a G_{3-a}-Si-(-OSiG_2)_n-(-OSiG_b(R_1)_{2-b})_m-O-SiG_{3-a}(R_1)_a$ (I)

wherein G is methyl; a is an integer of 1; b is 0, 1 or 2, preferably 1; n is a number from 400 to about 600; m is an integer of 0; $R_1$ is a monovalent radical conforming to the general formula $C_qH_{2q}L$, wherein q is an integer of 3 and L is $-NH_2$ Definitions of Components

*1 Polydimethylsiloxane, having a viscosity 10,000 mPa·s

*2 Available from Momentive having a viscosity 10,000 mPa·s, and having following formula (I):

$(R_1)_a G_{3-a}-Si-(-OSiG_2)_n-(-OSiG_b(R_1)_{2-b})_m-O-SiG_{3-a}(R_1)_a$ (I)

wherein G is methyl; a is an integer of 1; b is 0, 1 or 2, preferably 1; n is a number from 400 to about 600; m is an integer of 0; $R_1$ is a monovalent radical conforming to the general formula $CqH_{2q}L$, wherein q is an integer of 3 and L is $-NH_2$ Method of Preparation The above hair care compositions of "Ex. 1" through "Ex. 9" of the present invention and "CEx. i" through "CEx.vii" as comparative examples can be prepared by any conventional method well known in the art.

Properties and Benefits

For some of the compositions, some benefits are evaluated by the following methods. Results of the evaluation are shown above in Table.

Examples 1 through 9 are hair conditioning compositions of the present invention which are particularly useful for rinse-off use. The embodiments disclosed and represented by the previous "Ex. 1" through "Ex. 9" have many advantages. For example, they provide reduced crystallization of the solid organic compounds. Also, a comparison between "Ex. 1" and "CEx.i" and another comparison between "Ex. 2" and "CEx.ii" are both showing that the compositions of the present invention "Ex. 1" and "Ex. 2" provide improved deposition of the solid organic compounds. Furthermore, a comparison between "Ex. 1" and "CEx.iii and/or CEx.iv" shows that the compositions of the present invention "Ex. 1" provide reduced crystallization of the solid organic compounds while not deteriorating free flowing.

Deposition Test

The on-scalp deposition of the anti-dandruff active is measured by washing the hair and scalp of individuals. First, a shampoo is applied to the hair and scalp, and washed away. Then, one of the compositions of the above examples is applied, and rinsed off. The hair is parted on an area of the scalp to allow an open-ended glass cylinder to be held on the surface while an aliquot of an extraction solution is added and agitated prior to recovery and analytical determination of Piroctone Olamine content by conventional methodology, such as HPLC.

Free Flow—Pendulum

Free flow is measured by a pendulum measurement which detects degree of swinging of hair. More swinging means more free flowing. Treated hair is placed and a sensor to measure a degree of swinging is also placed. Same degree of starting force is given to the treated hair so that the treated hair starts swinging. The degree of swinging is measured during swinging, and shown as "pendulum area load".

(i) Preparation of Hair Switch

For the pendulum measurement, 20 grams hair switch with a length of 10 inch are used. The hair switches are prepared by following steps:
(1) The hair switches are bleached and combed in the same way. Then, applying 1.0 cc of non-conditioning shampoo per one hair switch, lathering, rinsing and drying the hair switches;
(2) Applying a non-conditioning shampoo at a level of 1.0 cc per one hair switch and lathering the hair switch; and rinsing the hair switch; and
(3) Applying conditioner at a level of 4.0 cc per hair switch for conditioner and treating the hair switch; and
(4) rinsing the hair switch;
(5) Then drying the hair switch at 23° C. and in low humidity (45%) environment overnight; and
(6) Hair switches are ready for pendulum measurements.

(ii) Evaluation

The above measurement in the step (ii) are conducted on at least 3 different hair switches prepared by the step (i) per one conditioner, and then calculate an average.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioning composition, comprising by weight:
(a) 0.1% to 4% of behenyl trimethyl ammonium methosulfate;
(b) about 1.5% to about 8% of a high melting point fatty compound selected from stearyl alcohol and cetyl alcohol;
(c) about 0.2% to about 1.0% of a solid organic compound selected from piroctone, piroctone olamine, ciclopirox, ciclopirox olamine, ergocalciferol and combinations thereof;
(d) about 0.3% to about 2% of a mixture of two or more first liquid oily compounds selected from the group consisting of isoropyl n-lauroyl sarcosinate, dihydro myrcenol, hexyl cinnamic aldehyde, hexyl salicylate, galoxolide, methyl dihydro jasmonate, linalool and limonene, wherein the mixture of first liquid oily compounds has a water solubility of 10 g per liter of water or less and a di-electric constant of 5 to 10, and wherein the weight ratio of the solid organic compound to the first liquid oily compounds is 1:1 to 1:10; and
(e) an aqueous carrier,
wherein the composition comprises 0.01% to 0.1% of a second liquid oily compound having an AlogP of 7.0 or higher, and
wherein the solid organic compound does not form crystals in the composition at 25° C.

2. The composition of claim 1, wherein the composition comprises 0.01% to 0.05% of the second liquid oily compound.

3. The composition of claim 1, the mixture of all the first liquid oily compounds included in the composition has a di-electric constant of 6 to 9.

4. The composition of claim 3, the mixture of all the first liquid oily compounds included in the composition has a di-electric constant of 7 to 9.

5. The composition of claim 1, wherein the weight ratio of the cationic surfactant to the high melting point fatty compound is in the range of about 1:1 to about 1:4.

6. The composition of claim 5, wherein the weight ratio of the cationic surfactant to the high melting point fatty compound is in the range of about 1:1.5 to about 1:3.5.

7. The composition of claim 1, wherein the composition comprises from about 0.22% to about 1.0% of the solid organic compound.

8. The composition of claim 1, wherein the weight ratio of the solid organic compound to the first liquid oily compound is 1:1.2 to 1:10.

9. The composition of claim 8, wherein the weight ratio of the solid organic compound to the first liquid oily compound is 1:1.5 to 1:10.

10. The composition of claim 1, wherein the composition further comprises about 0.1% to about 2% of a third liquid compound having an AlogP of about 1 to about 6.0 and a water solubility of 10 g per liter of water to about 50 g per liter of water.

11. The composition of claim 1, wherein the solid organic compound is selected from piroctone, piroctone olamine and mixtures thereof.

* * * * *